United States Patent [19]

Larock

[11] 4,119,642

[45] Oct. 10, 1978

[54] BUTENOLIDE SYNTHESIS VIA CARBONYLATION OF VINYLMERCURIALS IN THE PRESENCE OF INORGANIC SALTS

[75] Inventor: Richard Craig Larock, Ames, Iowa

[73] Assignee: Iowa State University Research Foundation, Inc., Ames, Iowa

[21] Appl. No.: 743,228

[22] Filed: Nov. 19, 1976

Related U.S. Application Data

[63] Continuation-in-part of Ser. No. 616,436, Sep. 24, 1975, Pat. No. 4,010,170.

[51] Int. Cl.$^2$ .................. C07D 307/58; C07D 307/94
[52] U.S. Cl. .................................................. 260/343.6
[58] Field of Search ...................................... 260/343.6

*Primary Examiner*—Norma S. Milestone
*Attorney, Agent, or Firm*—Zarley, McKee, Thomte, Voorhees & Sease

[57] ABSTRACT

Compounds containing the butenolide ring have a wide variety of chemical uses. The invention is an improved method of synthesizing β-halobutenolides which are valuable intermediates in preparing a variety of butenolide ring containing compounds. The method comprises reacting an acetylenic alcohol with a mercuric halide to provide a vinylmercuric halide and carbonylating the vinylmercuric halide in the presence of a basic inorganic salt to provide a β-halobutenolide.

9 Claims, No Drawings

BUTENOLIDE SYNTHESIS VIA CARBONYLATION OF VINYLMERCURIALS IN THE PRESENCE OF INORGANIC SALTS

CROSS REFERENCE TO A RELATED APPLICATION

This application is a continuation in part of Larock, Butenolide Synthesis via Carbonylation of Vinylmercurials, Ser. No. 616,436, filed Sept. 24, 1975 now U.S. Pat. No. 4,010,170.

BACKGROUND OF THE INVENTION

Compounds containing the butenolide ring which has the basic formula:

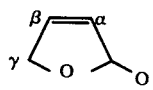

occur widely in nature and often possess an unusual range of biological activities. They appear throughout the plant kingdom from the simple metabolites of lichens, mold and fungi, to the more complex sesquiterpenes of the family Compositae and steriodal glycosides of the families Ranunculaceae, Liliaceae, Scrophullariaceae, and Apocyanaceae. More recently butenolides have been observed in such diverse animal species as sponges, and insects. In the latter species they may play a significant role as chemical defense weapons.

Certain butenolide ring containing compounds are useful as insecticides, herbicides, and seed and plant growth regulators. Of considerable importance also is the widespread characteristic among butenolide containing compounds of allergenic, antibacterial, and antifungal activity.

Undoubtedly, Vitamin C is the most physiologically important butenolide ring containing compound. Other uses for certain butenolide ring containing compounds include recently reported uses of cardiac glycosides as having the unusual characteristics of reducing the frequency of the heartbeat but increasing the amplitude of the heartbeat.

The unusual range of usefulness of compounds containing the basic butenolide ring has stimulated considerable research on the synthesis of these valuable compounds. While numerous methods have been reported in the literature for the preparation of butenolides, see for example, Y. S. Rao, *Chem. Rev.* 64, 353 (1964); W. E. Epstein and A. C. Sonntag, *J. Org. Chem.*, 32, 3390 (1967); K. Iwai, M. Kawai, H. Kosugi and H. Uda, *Chem. Lett.*, 385 (1974); and K. Iwai, H. Kosugi and H. Uda, *Chem. Lett.*, 1237 (1974), these methods all generally suffer from several disadvantages. Some of these disadvantages include inaccessibility of the starting materials, the necessity for employing severe reaction conditions, the very low yields of product obtained, and generally limited versatility in preparing the desired butenolide ring containing compounds.

The major objectives of the process of my earlier filed application, Ser. No. 616,436, were to provide a general synthesis route for a wide variety of butenolide compounds, to avoid the use of hydrogenation techniques and Grignard reagents, to provide a convenient two step synthesis for β-halobutenolides and to provide a process which provided high yields of the desired butenolides.

The reaction provided in my earlier invention could be conducted either in the presence of reaction equivalent amounts of noble metal salts or in the presence of catalytic amounts of noble metals.

It has now been found that the process of my earlier invention can be improved, from the standpoint of yield, particularly where the catalytic addition reaction is employed; and particularly where the trans-vinyl mercuric halide, employed in the second step reaction has a secondary or tertiary alcohol substitution, as distinguished from use of simple propargyl alcohol to prepare a trans-vinyl mercuric compound wherein R and R' are hydrogen, and the alcohol is therefore a primary one.

SUMMARY OF THE INVENTION

In its simplest terms, the process improvement is accomplished by the addition of basic inorganic salts to the vinylmercurial during the carbonylation reaction. More broadly, the invention relates to an improved method of synthesis of butenolide ring containing compounds, particularly, the invention relates to a new convenient synthesis method for preparation of β-halobutenolides. The improved process has particular applicability in preparing gamma substituted β-halobutenolides in high yields.

DETAILED DESCRIPTION OF THE INVENTION

In the first step of the process of this invention, an acetylenic or more specifically a propargylic alcohol of the formula:

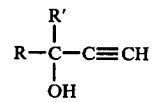

is reacted with a mercuric halide, of the formula: $HgX_2$ wherein X is selected from the group consisting of halides and is preferably chloride.

As can be seen from the above general formula for the acetylenic alcohol, when R and R' are hydrogen, the acetylenic alcohol is propargyl alcohol. From time to time the term "substituted acetylenic alcohol" will be utilized herein and it is understood that what is meant is propargyl alcohol wherein the hydrogen moieties for R and R' are substituted with alkyl or other appropriate groups as hereinafter explained.

The first step reaction may be represented by the following equation:

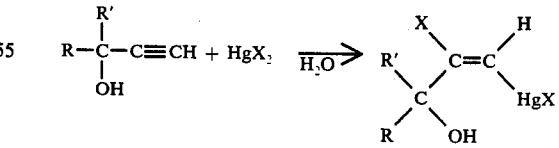

As can be seen from the immediately preceding equation, the acetylenic alcohol is reacted with mercuric chloride to provide a vinylmercuric chloride, and wherein R and R' are hydrogen with the starting acetylenic alcohol being a propargyl alcohol, the product of the first step reaction is a trans-vinylmercuric chloride.

As can be appreciated, since the reaction of the acetylenic alcohol and the mercuric chloride is an equimolar addition reaction, it is preferred that at least equimolar amounts of each reactant be employed. It is also preferred that this reaction be conducted in an aqueous medium.

It is preferred that the mercuric halide be mercuric chloride because of its ease of solubility. Most preferably, this first step reaction, set forth above, is conducted utilizing mercuric chloride in an aqueous medium which is comprised of a saturated solution of mercuric chloride in a sodium chloride solution in order to enhance the solubility characteristics of mercuric chloride. It is also preferred that the reaction be conducted in the presence of an excess of mercuric chloride in order to insure that the reaction is carried to completion.

No criticality exists with regard to the temperature employed during this first step reaction; however, for convenience purposes, it is preferred that the reaction be conducted at room temperature. In addition, there is no criticality with regard to the pressures employed during this first step reaction and preferably the pressure is simply atmospheric pressure. Likewise, there is no criticality with regard to the time of reacting for this first step reaction since the reaction is substantially instantaneous addition reaction.

In a second step reaction, the vinylmercuric halide, or in the case where R and R' of the acetylenic alcohol are something other than hydrogen, a substituted vinylmercuric halide is carbonylated according to the following equation:

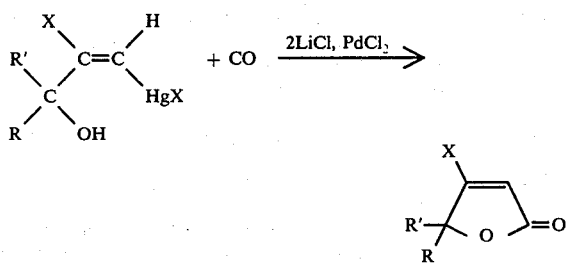

As can be seen, the carbonylation reaction involves a removal of the mercuric chloride moiety, HgX, from the vinylmercuric halide and the addition of the carbonyl group at the same situs followed by an internal esterification reaction closing the ring and forming the butenolide ring containing compound.

As shown in the example of my earlier application, where R and R' are hydrogen very satisfactory high yields of the desired $\beta$-halobutenolide were obtained. However, it has now been found that where R or R' are not hydrogen, so that the alcoholic moiety of the trans-vinylmercuric halide in either secondary or tertiary, the yields were considerably lower. The yields are significantly increased by the addition of a basic, inorganic salt to the second step reaction. The preferred salts are alkali metal and alkaline earth metal oxides and carbonates. Preferably lithium, sodium, potassium, magnesium, calcium or barium salts are employed, with magnesium or potassium salts being preferred.

As mentioned previously to obtain increased reaction yield benefits, the salt must be a basic salt. The most preferred salts are magnesium oxide and potassium carbonate.

It is not known precisely why the salt addition improves the reaction yields, but it is believed that the basic salt reacts with hydrochloric acid formed during the second step reaction, and prevents the acid from being available to promote undesired side reactions rather than the desired butenolide formation.

The amount of salt to be added is preferably a reaction equivalent amount although the amount is not critical and may be more or less.

The carbonylation reaction is preferably conducted in the presence of either a reaction equivalent amount of a noble metal salt and lithium chloride or alternatively and most preferably, is a palladium catalyst promoted carbonylation reaction conducted in the presence of a reoxidant such as cupric chloride. However, it is to be understood that other noble metals can be utilized with equally satisfactory results. For example, platinum, iridium, rhodium, ruthenium and the like. Where the noble metal salt promotion is utilized, lithium chloride is thereafter involved in an exchange reaction with the palladium salt. Where the noble metal catalyst is employed the noble metal catalyst is either the noble metal on charcoal or a halide salt of a noble metal, for example, palladium chloride. Typically, in the catalytic promotion about 1% by weight of the catalyst is employed and two equivalents of the cupric chloride reoxidant are employed to reoxidize $Pd^0$ to $Pd^{2+}$. In summary, the carbonylation reaction is promoted by noble metals. Noble metal salts in combination with lithium chloride may be employed at reaction equivalent levels or alternatively, catalytic amounts of the noble metal or its halide salts may be employed in the presence of a reoxidant such as cupric chloride.

While improved yields are obtained when either the noble metal salts in combination with reaction equivalent levels of lithium chloride are used with the basic salt addition technique, or where the catalytic amounts of noble metals are employed, the greatest reaction yield improvements are seen when the catalytic addition reaction is employed. It is therefore most highly preferred that the improved process of this invention be employed in combination with the second step carbonylation reaction of my earlier invention whenever the second step carbonylation is catalytically promoted.

The above discussed carbonylation reaction is preferably conducted in the presence of a polar organic solvent that is inert to the reactants employed in the carbonylation reaction, i.e., carbon monoxide and the vinylmercuric halide. The precise polar organic solvent employed is not critical and any of the conventional ones may be utilized such as ethyl alcohol, methyl alcohol, ether, acetone and the like. It should, however, be understood that while the utilization of an organic polar solvent in the carbonylation-lactonization second-step reaction is preferred, if desired, the reaction can be carried out in the presence of aqueous solvent medium.

It is preferred that the carbonylation reaction be conducted by adding the noble metal halide, the lithium chloride, and the polar organic solvent together in a reaction flask. Thereafter, the reaction mixture may be cooled to low temperatures, as low as $-78°$ C., if desired, and purged with a carbon monoxide atmosphere. While purging with carbon monoxide is occurring the vinylmercuric halide is added. After the entire amount of the vinylmercuric halide is added to the reaction mixture, the reaction is thereafter allowed to gradually rise to room temperature. While low temperatures in the neighborhood of $-20°$ C. to $-78°$ C. are preferred, it should be understood that they are not critical and that the reaction can equally as well be carried out under ambient conditions.

As can be seen from an examination of both of the reaction steps set forth above, i.e., the first step reaction of an acetylenic alcohol with a mercuric halide, followed by the second step of carbonylating the resulting vinylmercuric halide in the presence of a noble metal catalyst to provide a butenolide ring containing compound, the R and R' substituents on the acetylenic alcohol ultimately become gamma position moieties on the butenolide ring, after the carbonylation reaction occurs. Thus the precise value of R and R' for the acetylenic alcohol will depend upon what organic moieties are selected for the gamma position substituents on the butenolide compound. For example, where R and R' are hydrogen, the starting acetylenic alcohol is propargyl alcohol and the resulting butenolide compound is B-chloro-butenolide. Thus, there is no precise criticality with regard to the substituents R and R' and they are in fact selected to build the desired butenolide ring containing compound for ultimate usage. Preferably, however, R and R' are selected from the group consisting of hydrogen, alkyls, aryls, substituted alkyls, substituted aryls, aralkyls and substituted aralkyls. For example, R and R' can be the following:

| R | R' |
|---|---|
| H | H |
| $CH_3$ | $CH_3$ |
| $CH_3$ | $C_2H_5$ |
| $-(CH_2)_4-$ | |
| $-(CH_2)_5-$ | |

As previously mentioned, the butenolide ring containing compounds have a variety of uses and the precise compound ultimately prepared will determine the values for the R and R' moieties of the acetylenic alcohol utilized in the first reaction discussed above. For example, the following table lists several known useful butenolide ring containing compounds which can be prepared by appropriate selection of R and R'.

pound has a beta chlorine moiety. Since most butenolide ring containing compounds which are known to possess valuable properties do not contain a beta chloride moiety, in many instances it is necessary to remove the beta position chloride moiety. This can be done with a wide variety of reducing agents. For example, $H_2$—Pd/C—HOAc—NaOAc, Li—t—$C_4$-$H_9$OH—THF, Na(Hg), Na—$NH_3$, Na—t—$C_4$-$H_9$OH—THF, Na-naphthalene, Mg—i—$C_3H_7$OH, Zn—HOAc, Zn(Ag)—$CH_3$OH, $CrSO_4$—DMF, $Cr(ClO_4)_2$—EDA, $NaBH_4$—$H_v$, $NaBH_4$—$PdCl_2$, $LiHAl(OCH_3)_3$—CuI, and $Li(n-C_4H_9CuH)$. The most preferred reducing agent is: Zn(Ag)—$CH_3$OH. Of course, if desired, the beta chlorine position can be reduced to provide a hydrogen in this position or alternatively it provides an ideal site for an additional alkyl substitution. Thus, for example, a number of extremely important compounds most notably aglycones of the cardiac glycosides (cardenolides) possess alkyl substituents in the beta position. Treatment of the beta chlorobutenolide with organocopper reagents will provide a broad array of such beta-substituted compounds. Such copper promoted alkylation reactions are already well known in other organic syntheses and will therefore not be described in detail herein. However, for further reference with regard to copper promoted alkylation reactions, See Posner, "Organic Reactions", J. Wiley, New York, which to the extent that it deals with copper alkylation reactions is incorporated specifically herein by reference.

The following examples are offered to further illustrate but not limit the invention disclosed herein.

EXAMPLE 1

Propargyl alcohol having the empirical formula HO—$CH_2$C ≡ CH was reacted with mercuric chloride in an aqueous solvent medium. The first step reaction was conducted in the following manner. A 50 milliliter saturated solution of sodium chloride and mercuric

| Butenolide Ring Containing Compound | Use | Value of R & R' Substituents on the Acetylenic Alcohol |
|---|---|---|
| [structure with R group] | Seed and plant growth regulators; also tobacco flavor and aroma ingredient. | R=$CH_3$ or $C_2H_5$<br>R'=H |
| [structure with $CH_3$ and long chain] | Insecticide | R=$CH_3$ also substituted<br>R'=H at B position |
| [structure with $CH_2$=CH] | Useful annelation reagent for the synthesis of tumor inhibiting sesquiterpene lactones | R=H; R'=H<br>β=$CH_2$=CH (β substituted) |
| [structure with $(CH_3)_2$CH] | Tobacco flavor and aroma ingredient | R and R'=H ; substituted at B position with isopropyl |
| [structure with $CH_3CH_2$] | Appears in raspberry oil; useful flavor and aroma ingredient | R'=H<br>R=$C_2H_5$; also see first listing in table |

As seen from the previously described carbonylation equation, the resulting butenolide ring containing comchloride was prepared at ambient temperatures. Sodium chloride was utilized in combination with mercuric chloride in order to increase the solubility of the mercuric chloride. The solution was thereafter cooled while 10 grams of propargyl alcohol was dripped in with rapid stirring. The reaction mixture turned completely solid, was filtered and washed with cold water, and then recrystallized from benzene to provide trans-2-chloro-3-hydroxy-1-propenyl-mercuric chloride in 88% of theoretical yield. The vinylmercuric chloride is shown in the first shown reaction wherein R and R' are hydrogen.

Thereafter the carbonylation reaction was conducted in the following manner. Anhydrous lithium chloride (20 mmol), anhydrous cupric chloride (20 mmol) and palladium chloride (0.1 mmol) and 100 ml. of ether were added to a well dried 250 ml round bottom flask containing a septum inlet and carbon monoxide inlet tube. The flask was cooled to −78° C. and 10 mmol of trans-2-chloro-3-hydroxy-1-propenyl mercuric chloride was added. The flask was flushed thoroughly with carbon monoxide and the well-stirred reaction mixture was then allowed to slowly warm to room temperature over a 4 hour period. It was thereafter stirred overnight while maintaining a slight positive pressure of carbon monoxide. Ether and activated carbon were added to the reaction mixture which was filtered, washed with saturated ammonium chloride and dried over anhydrous sodium sulfate.

Filtration and evaporation of the solvent gave an isolated yield of β-chlorobutenolide of 96% of theoretical. Melting point analysis of the β-chlorobutenolide showed a melting point within the range of 52.5° to 53° C.

Thereafter the β-chlorobutenolide was treated with a dimethyl cuprate reagent. Two equivalents of methyl lithium were added to one equivalent of cuprous iodide-tributyl phosphine complex at 0° C. and the reaction mixture was cooled to −78° C. The β-chlorobutenolide was added and stirred over a 10 minute period after which the reaction mixture was quenched with ammonium chloride solution. The resulting compound had the β-chloro moiety removed and a methyl group substituted to provide β-methyl-Δα,β, butenolide.

When in the above example the carbonylation reaction was promoted by the use of 10 mmol. of palladium chloride and no cupric chloride was employed as a reoxidant, substantially similar results were obtained.

The above example shows that where R and R' are hydrogen the carbonylation reaction of my earlier invention provides the desired butenolide at very high yields. As seen by the examples below, similar high yields are obtained where R and R' are not hydrogen when the basic salt addition technique of this invention is employed.

EXAMPLES 2-6

Lithium chloride (10 mmol), palladium chloride (5 mmol) magnesium oxide (5 mmol) and 50 ml THF were placed in a round bottom flask with a septum inlet. After flushing with carbon monoxide and cooling to −78° C., the vinylmercurial (5 mmol) was added. A balloon filled with carbon monoxide was connected to the top of the flask and the reaction mixture was allowed to warm to 0° C. and stirred 24 hours at that temperature. Five ml. saturated ammonium chloride solution, 50 ml ether and charcoal were added. The mixture was stirred an additional 30 minutes and then filtered. The filtrate was washed with saturated potassium carbonate solution and dried over anhydrous sodium sulfate. Filtration, evaporation and recrystallization (Pentane) provided the isolated yields indicated in the table. Yields determined by GLC were run in an identical manner on one fifth this scale using an appropriate hydrocarbon internal standard.

TABLE

Synthesis of β-chloro-Δ", β-butenolides

| Example No. | Vinylmercurial | MP(° C)" | | MP (° C)" | % Yield" |
|---|---|---|---|---|---|
| 1. | 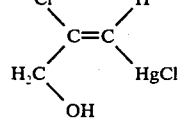 | 105(105) | 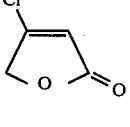 | (52.5–53) | (96) |
| 2. | 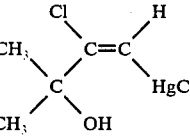 | 78(70) | 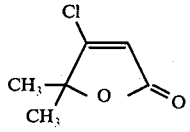 | 66–66.5 | 100(88) |
| 3. | 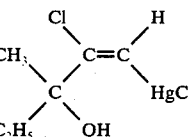 | 85–86 | 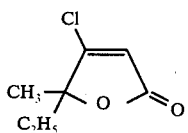 | −5 | 91 |
| 4. | 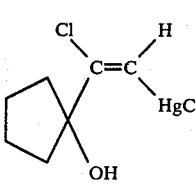 | 99–100 | 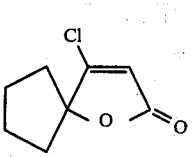 | 36–36.5 | 99 |

TABLE-continued

Synthesis of β-chloro-Δ^α,β-butenolides

| Example No. | Vinylmercurial | MP(° C)^a | | MP (° C)^a | % Yield^b |
|---|---|---|---|---|---|
| 5. | (structure with cyclohexyl, C=C, Cl, H, HgCl, OH) | 137–138 | (structure with cyclohexyl spiro butenolide, Cl) | 55–55.5 | 100(92) |
| 6. | (structure with CH₃ groups, Cl, C=C, OH, HgCl) | (103) | (structure with CH₃ groups, Cl, butenolide, OH) | 102 | 94 |

^a Observed melting point (literature melting point)
^b Yield determined by GLC (isolated yield).

EXAMPLES 7–10
General Catalytic Procedure

Palladium chloride (0.01 or 0.10 mmol), anhydrous cupric chloride (2 mmol), magnesium oxide (1 mmol) and 5 ml. benzene were placed in a round bottom flask with a septum inlet. After flushing with carbon monoxide, the vinylmercurial (1 mmol) and 5 ml benzene were added. A balloon filled with carbon monoxide was connected to the top of the flask, and the mixture was stirred at warm room temperature (~35° C.) for 2 or 3 days. Addition of an appropriate internal standard and gas chromatographic analysis gave the yields indicated in the table.

TABLE

| Example No. | Butenolide | % Yield (1% PdCl₂) | % Yield (10% PdCl₂) |
|---|---|---|---|
| 7. | (Cl, CH₃, CH₃ butenolide) | 99 | 100 |
| 8. | (Cl, CH₃, CH₃CH₂ butenolide) | 57 | 100 |
| 9. | (cyclohexyl spiro Cl butenolide) | 54^a | 100 |
| 10. | (cyclopentyl spiro Cl butenolide) | 83 | 84^a |

^a Impure organomercurial used.

In the above Examples 7, 8, 9 and 10, when the processes are repeated without the addition of magnesium oxide, yields are substantially reduced. For example, when Example 9 was run, utilizing the 10% palladium chloride catalyst, without the addition of magnesium oxide, a yield of only 62% was obtained. Whereas, when magnesium oxide was utilized, the yield was 100%.

EXAMPLES 11–20

When the process of Examples 2 through 6 was repeated for the following vinylmercuric halide carbonylation:

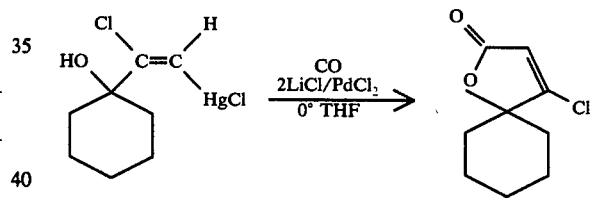

utilizing differing basic metal salts, the percentage yields shown in the table below were obtained:

TABLE

| METAL SALT | % YIELD |
|---|---|
| K₂CO₃ | 96 |
| MgO | 95 |
| CaO | 95 |
| CaCO₃ | 88 |
| Li₂CO₃ | 87 |
| BaO | 83 |
| Al₂O₃ | 79 |
| NaOAc | 76 |
| Na₂SO₄ | 66 |
| MgSO₄ | 61 |
| — | 58 |

In the above examples one equivalent of basic metallic salt was utilized per one equivalent of vinylmercuric chloride compound.

What is claimed is:

1. A method of preparing β-halobutenolide, and gamma substituted derivatives thereof, said method comprising, reacting a compound of the formula:

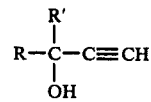

wherein R and R' are organic moieties selected to represent the gamma substituents of the particular butenolide being prepared, with a mercuric halide to provide a vinylmercuric halide, and carbonylating said vinylmercuric halide, in the presence of a carbonylating agent selected from the group consisting of noble metals and noble metal salts, and in the presence of a basic inorganic metal salt selected from the group consisting of Group I and Group II metal salts, and aluminum oxide to provide β-halobutenolide or a gamma substituted derivative thereof.

2. The method of claim 1 wherein R and R' are selected from the group consisting of alkyl, aryl, substituted alkyl, substituted aryls, aralkyls, and substituted aralkyls.

3. The method of claim 1 wherein said mercuric halide is mercuric chloride.

4. The method of claim 3 wherein said mercuric halide is reacted with said compound of the formula:

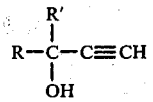

in an aqueous solvent.

5. The method of claim 4 wherein said aqueous solvent includes dissolved sodium chloride.

6. The method of claim 5 wherein said carbonylating occurs in the presence of a noble metal catalyst.

7. The method of claim 6 wherein said carbonylating occurs in the presnce of a polar organic solvent which is inert to the reaction ingredients.

8. A method of preparing β-halobutenolides from a trans-2-halo-3-hydroxy-1-propenyl-mercuric halide, or substituted derivatives thereof, said method comprising, carbonylating said trans-2-halo-3-hydroxy-1-propenyl-mercuric halide, or a substituted derivative thereof in the presence of a basic inorganic metal salt selected from the group consisting of Group I and Group II metal salts and aluminum oxide and a carbonylating agent selected from the group consisting of the noble metals and noble metal salts, to provide β-halobutenolides.

9. The method of claim 1 wherein said salt is selected from the group consisting of magnesium oxide and potassium carbonate.

* * * * *